United States Patent
Wiesman

(10) Patent No.: US 10,632,272 B2
(45) Date of Patent: Apr. 28, 2020

(54) SURGICAL AIRWAY DEVICE AND METHOD OF USE

(71) Applicant: Precision Ventures, LLC, Waltham, MA (US)

(72) Inventor: Joshua Wiesman, Weston, MA (US)

(73) Assignee: Precision Ventures, LLC, Waltham, MA (US)

( * ) Notice: Subject to any disclaimer, the term of this patent is extended or adjusted under 35 U.S.C. 154(b) by 821 days.

(21) Appl. No.: 15/153,109

(22) Filed: May 12, 2016

(65) Prior Publication Data
US 2016/0256652 A1 Sep. 8, 2016

Related U.S. Application Data

(63) Continuation of application No. PCT/US2014/014448, filed on Feb. 3, 2014.
(Continued)

(51) Int. Cl.
*A61M 16/04* (2006.01)
*A61M 16/08* (2006.01)
(Continued)

(52) U.S. Cl.
CPC ......... *A61M 16/0493* (2014.02); *A61B 5/082* (2013.01); *A61M 16/0463* (2013.01);
(Continued)

(58) Field of Classification Search
CPC .. A61M 16/00; A61M 16/04; A61M 16/0463; A61M 16/0475;
(Continued)

(56) References Cited

U.S. PATENT DOCUMENTS

| 4,534,542 A | 8/1985 | Russo |
| 5,165,420 A * | 11/1992 | Strickland ........... A61M 1/0058 600/581 |

(Continued)

FOREIGN PATENT DOCUMENTS

WO 2014121199 A1 8/2014

OTHER PUBLICATIONS

The International Search Report and Written Opinion of the International Searching Authority dated Apr. 16, 2014 for corresponding PCT Application No. PCT/US14/14448.

*Primary Examiner* — Quang D Thanh
*Assistant Examiner* — Jacqueline M Pinderski
(74) *Attorney, Agent, or Firm* — Brian M. Dingman; Dingman IP Law, PC

(57) ABSTRACT

Featured herein is a surgical airway device (10) that is constructed and arranged to be placed into the mouth of a patient to maintain a surgical airway in the patient. Also featured is a method of using such a surgical airway device (10). The surgical airway device (10) has a flange (20) that is constructed and arranged to be located outside of the mouth, an inner tube (21) that defines a working channel (22) defining an anterior opening in the flange (20) and located proximate the lips, and a posterior end (26) located in the back of the mouth. There is an outer tube (70) that is generally coaxial with, spaced from and fully or partially surrounds the inner tube (21), wherein a coaxial gap (80) is located between at least part of the outer tube (70) and the inner tube (21). There is a first lumen (30) that is in fluid communication with the working channel (22) and a second lumen (40) that is in fluid communication with the coaxial gap (80).

22 Claims, 16 Drawing Sheets

Related U.S. Application Data

(60) Provisional application No. 61/759,644, filed on Feb. 1, 2013, provisional application No. 61/762,051, filed on Feb. 7, 2013.

(51) Int. Cl.

| | | |
|---|---|---|
| *A61M 25/02* | (2006.01) | |
| *A61B 5/08* | (2006.01) | |
| *A61B 5/087* | (2006.01) | |
| *A61B 1/267* | (2006.01) | |
| *A61B 5/097* | (2006.01) | |
| *A61B 5/083* | (2006.01) | |

(52) U.S. Cl.
CPC ...... *A61M 16/0495* (2014.02); *A61M 16/085* (2014.02); *A61B 1/267* (2013.01); *A61B 5/087* (2013.01); *A61B 5/0836* (2013.01); *A61B 5/097* (2013.01); *A61M 2025/022* (2013.01); *A61M 2202/0208* (2013.01); *A61M 2202/0466* (2013.01); *A61M 2230/432* (2013.01)

(58) Field of Classification Search
CPC ........... A61M 16/0477–0497; A61M 16/0495; A61M 16/08; A61M 16/0816; A61M 16/0841–0858; A61M 2202/0466; A61M 2202/0208; A61M 2230/432; A61M 2025/022; A61B 5/00; A61B 5/08; A61B 5/082; A61B 5/083–087; A61B 5/097; A61B 1/00; A61B 1/267

See application file for complete search history.

(56) References Cited

U.S. PATENT DOCUMENTS

| | | | | |
|---|---|---|---|---|
| 6,923,184 | B1* | 8/2005 | Russo | A61M 16/0463 128/200.26 |
| 8,220,461 | B1* | 7/2012 | Guerra | A61M 16/0463 128/200.26 |
| 2002/0053346 | A1* | 5/2002 | Curti | A61M 16/0666 128/207.18 |
| 2006/0272647 | A1* | 12/2006 | Hauge | A61M 16/0488 128/207.16 |
| 2007/0006878 | A1* | 1/2007 | Mackey | A61M 16/0488 128/200.26 |
| 2008/0110456 | A1 | 5/2008 | Flynn et al. | |
| 2010/0030027 | A1* | 2/2010 | Bastid | A61M 16/0488 600/120 |
| 2010/0317987 | A1* | 12/2010 | Inoue | A61M 16/0488 600/543 |
| 2011/0226239 | A1 | 9/2011 | Hauge | |
| 2012/0017917 | A1 | 1/2012 | Podmore et al. | |
| 2014/0144432 | A1* | 5/2014 | Avitsian | A61M 16/04 128/202.16 |

* cited by examiner

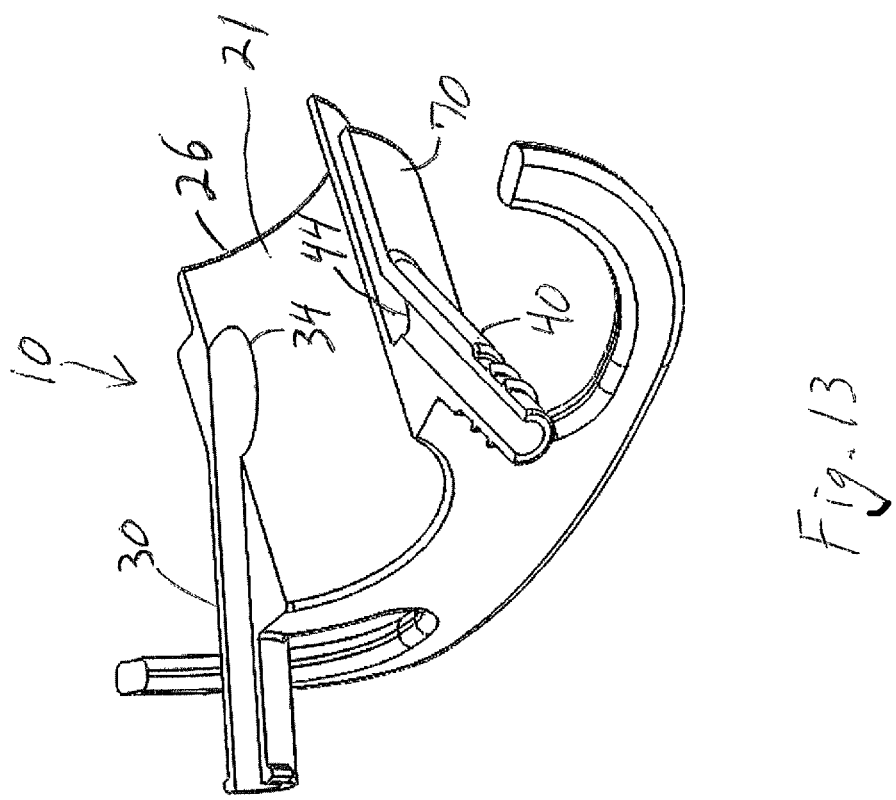

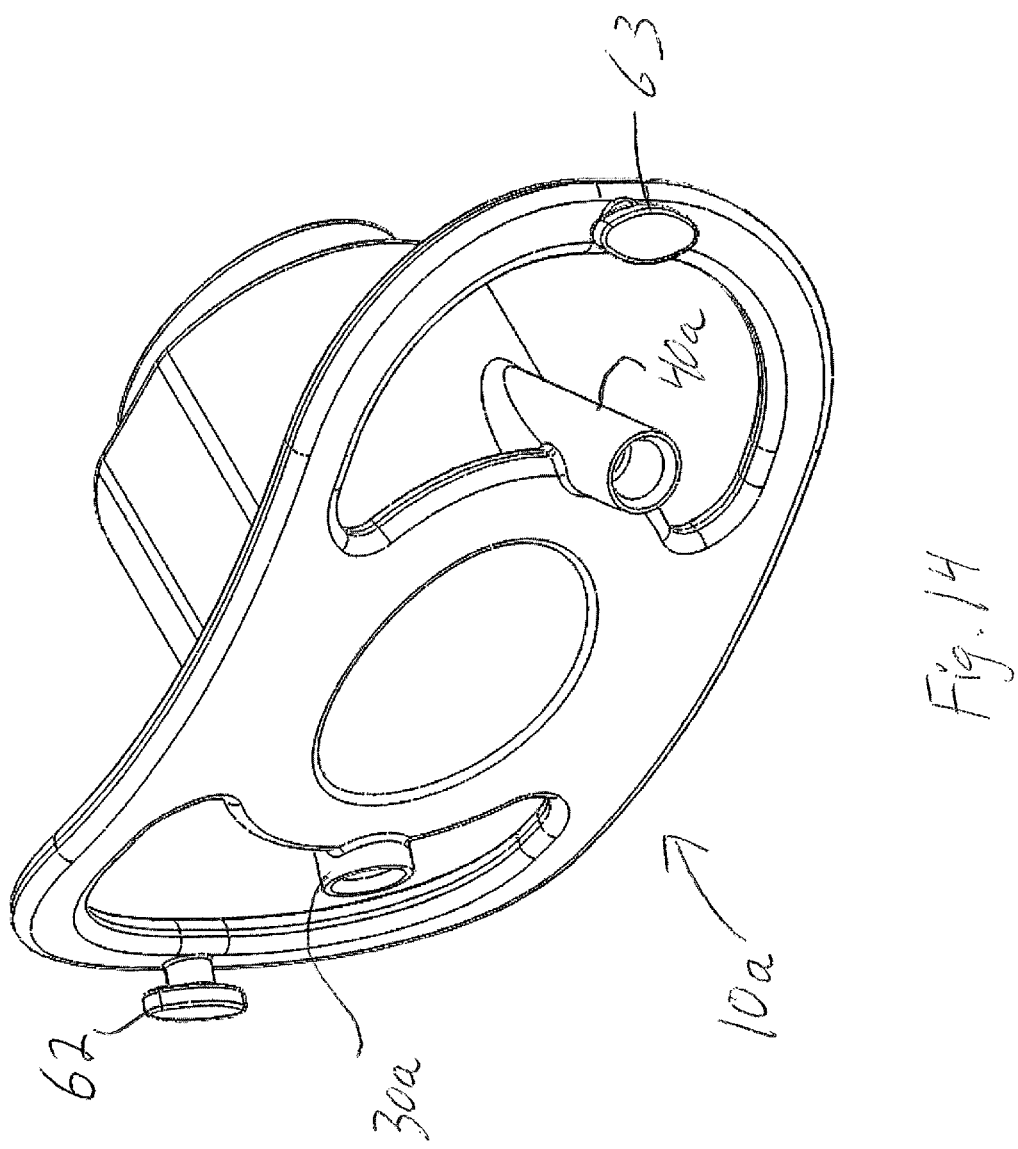

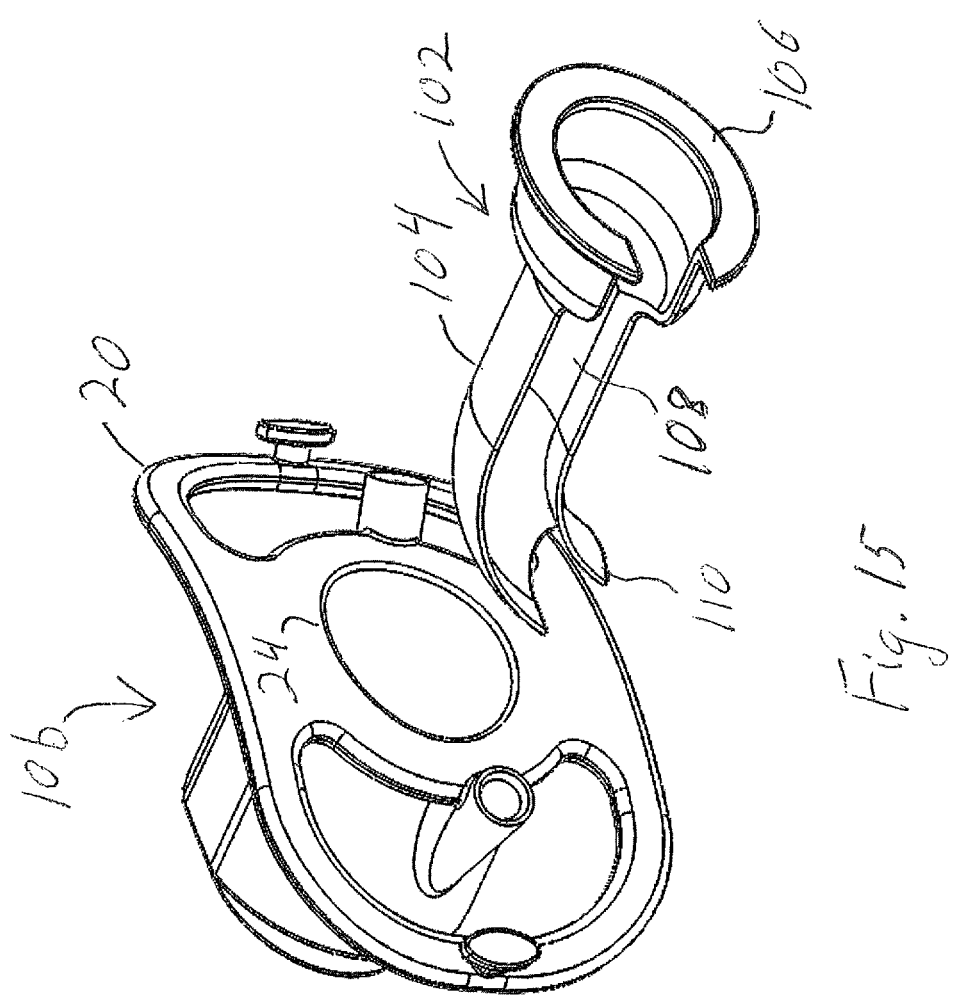

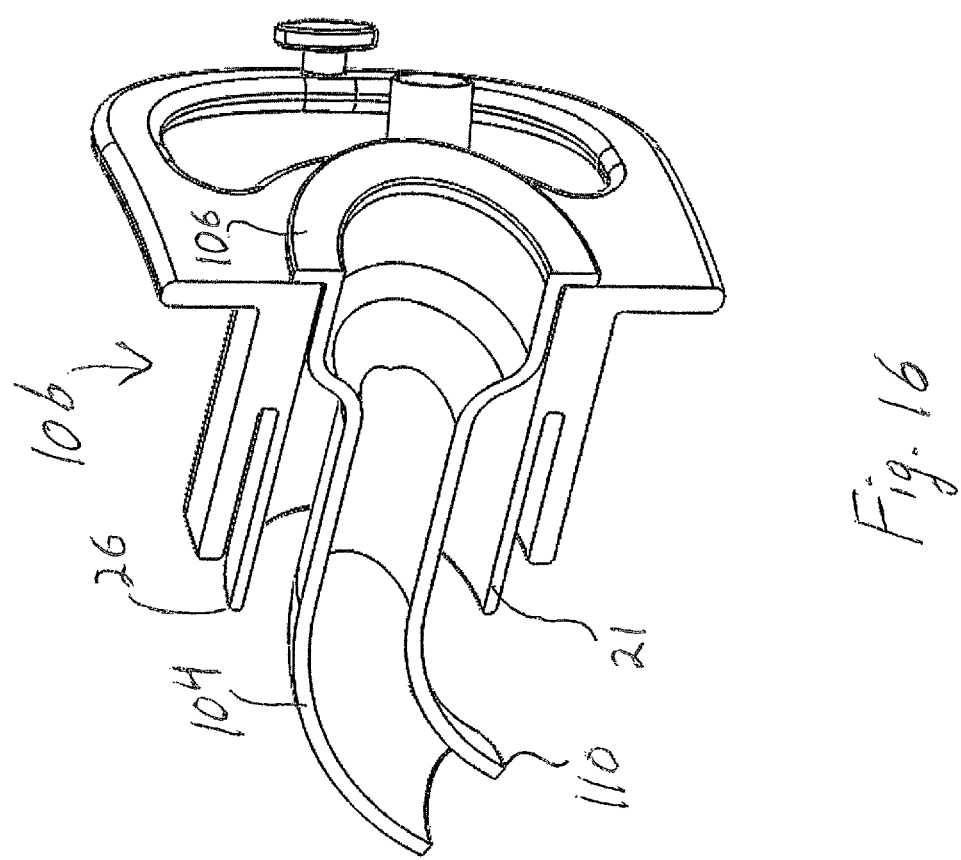

SURGICAL AIRWAY DEVICE AND METHOD OF USE

CROSS-REFERENCE TO RELATED APPLICATION

This application is a continuation of and claims priority of PCT/US2014/014448 filed on Feb. 3, 2014, which itself claimed priority of Provisional Patent Application 61/759,644 filed on Feb. 1, 2013, and Provisional Patent Application 61/762,051 filed on Feb. 7, 2013.

FIELD

This disclosure relates to an airway device that can be used during surgery or for outpatient procedures requiring sedation anesthesia.

BACKGROUND

Surgical airway devices are used to maintain an airway during surgeries or other procedures in which the patient is anesthetized. It is desirable for the airway device to provide a lumen through which a scope or other instrument can be inserted through the mouth, while also allowing for capnography and other types of patient monitoring.

SUMMARY

This disclosure features a surgical airway device that is constructed and arranged to be placed into the mouth of a patient, to maintain a surgical airway in the patient. The surgical airway device can include a flange constructed and arranged to be located outside of the mouth, an inner tube that defines a working channel defining an anterior opening in the flange and located proximate the lips, and a posterior end located in the back of the mouth, an outer tube that is generally coaxial with, spaced from and fully or partially surrounds the inner tube, wherein a coaxial gap is located between at least part of the outer tube and the inner tube, a first lumen that is in fluid communication with the working channel, and a second lumen that is in fluid communication with the coaxial gap.

The second lumen may be on the left side of the inner tube when the surgical airway device is placed in the patient's mouth. The second lumen may be adapted to be connected to at least one of a source of suction and a source of oxygen. The surgical airway device may further comprise a suction control device located between the second lumen and a source of suction. The first lumen may be on the right side of the inner tube when the device is placed in the patient's mouth. The first lumen may be adapted to be connected to a carbon dioxide monitor.

The surgical airway device may further comprise a curved wall bordering at least part of the coaxial gap, to help direct saliva into the second lumen or to help drive oxygen from the second lumen. The surgical airway device may define a lateral midline, and the two lumens may he located at or below the midline. The surgical airway device may further comprise a sheath located in the working channel and with an opening that is in fluid communication with the first lumen. The sheath may have a posterior end that projects beyond the posterior end of the inner tube. The sheath may have a sheath flange that sits against the flange of the surgical airway device, and a curved sheath tube that is located in the inner tube and has a posterior end that projects beyond the posterior end of the inner tube. The sheath opening may comprise an open side in the sheath tube, wherein the open side also extends through the sheath flange.

Also featured herein is a surgical airway device that is constructed and arranged to be placed into the mouth of a patient, to maintain a surgical airway in the patient, the surgical airway device comprising a flange constructed and arranged to be located outside of the mouth, an inner tube that defines a working channel defining an anterior opening in the flange and located proximate the lips, and a posterior end located in the back of the mouth, an outer tube that is generally coaxial with, spaced from and fully or partially surrounds the inner tube, wherein a coaxial gap is located between at least part of the outer tube and the inner tube, a first lumen that is in fluid communication with the working channel, wherein the first lumen is on the right side of the inner tube when the device is placed in the patient's mouth and wherein the first lumen is adapted to be connected to a carbon dioxide monitor, and a second lumen that is in fluid communication with the coaxial gap, wherein the second lumen is on the left side of the inner tube when the surgical airway device is placed in the patient's mouth and wherein the second lumen is adapted to be connected to at least one of a source of suction and a source of oxygen. The surgical airway device defines a lateral midline, and the two lumens are located at or below the midline.

The surgical airway device may further comprise a sheath located in the working channel and with an opening that is in fluid communication with the first lumen, wherein the sheath has a posterior end that projects beyond the posterior end of the inner tube.

Further featured herein is a method of accomplishing an airway, a scope working channel, at least one of posterior saliva suction and oxygen delivery, and anterior capnography in a patient, the method comprising: a) providing a surgical airway device for maintaining a surgical airway in a patient, the surgical airway device comprising i) a flange constructed and arranged to be located outside of the mouth, ii) an inner tube that defines a working channel defining an anterior opening in the flange and located proximate the lips, and a posterior end located in the back of the mouth; iii) an outer tube that is generally coaxial with, spaced from and fully or partially surrounds the inner tube, wherein a coaxial gap is located between at least part of the outer tube and the inner tube; iv) a first lumen that is in fluid communication with the working channel; and v) a second lumen that is in fluid communication with the coaxial gap; b) inserting the surgical airway device into the patient's mouth such that the flange is located outside of and against or very close to the lips; c) fluidly coupling a carbon dioxide monitoring device to the first lumen; and d) fluidly coupling a suction source or an oxygen delivery source to the second lumen.

The second lumen may be on the left side of the inner tube when the device is placed in the patient's mouth. The surgical airway device may further comprise a suction control device located between the second lumen and a source of suction. The first lumen may be on the right side of the inner tube when the surgical airway device is placed in the patient's mouth. The surgical airway device may further comprise a curved wall bordering at least part of the coaxial gap, to help direct saliva into the second lumen.

Still further featured herein is a method of accomplishing an airway, a scope working channel, at least one of posterior saliva suction and oxygen delivery, and anterior capnography in a patient, comprising a) providing a surgical airway device for maintaining a surgical airway in a patient, the surgical airway device comprising i) a flange constructed and arranged to be located outside of the mouth, ii) an inner tube that defines a working channel defining an anterior opening in the flange and located proximate the lips, and a posterior end located in the back of the mouth, iii) an outer tube that is generally coaxial with, spaced from and fully or partially surrounds the inner tube, wherein a coaxial gap is located between at least part of the outer tube and the inner tube, iv) a curved wall bordering at least part of the coaxial gap, to help direct saliva into the second lumen, v) a first lumen that is on the right side of the inner tube when the surgical airway device is placed in the patient's mouth and that is in fluid communication with the working channel, and vi) a second lumen that is on the left side of the inner tube when the device is placed in the patient's mouth and that is in fluid communication with the coaxial gap, b) inserting the surgical airway device into the patient's mouth such that the flange is located outside of and against or very close to the lips, c) fluidly coupling a carbon dioxide monitoring device to the first lumen, and d) fluidly coupling a suction source to the second lumen.

BRIEF DESCRIPTION OF THE DRAWINGS

Non-limiting embodiments of the device for maintaining a surgical airway are depicted in the drawings, in which:

FIG. 13 is a horizontal mid-line cross-sectional left front perspective view of the surgical airway device of FIG. 1.

FIG. 14 is a front view of an alternative surgical airway device.

FIG. 15 is a front exploded view of another alternative surgical airway device.

FIG. 16 is a vertical midline cross-sectional view of the surgical airway device of FIG. 15.

DETAILED DESCRIPTION

Figure 1:
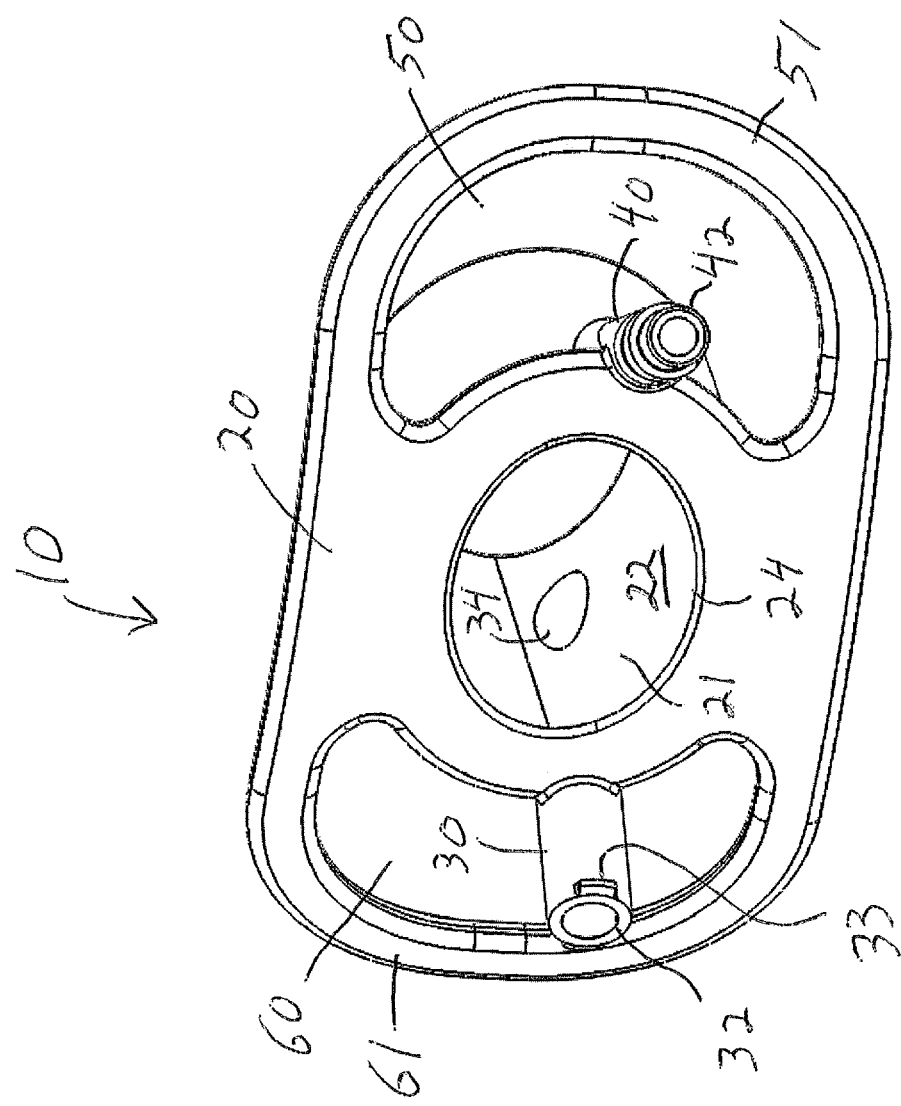
FIG. 1 is a left front perspective view of a surgical airway device that is constructed and arranged to be placed into the mouth of a patient. The device is used to maintain a surgical airway in the patient and to accomplish other functions as described below.
Figure 2:
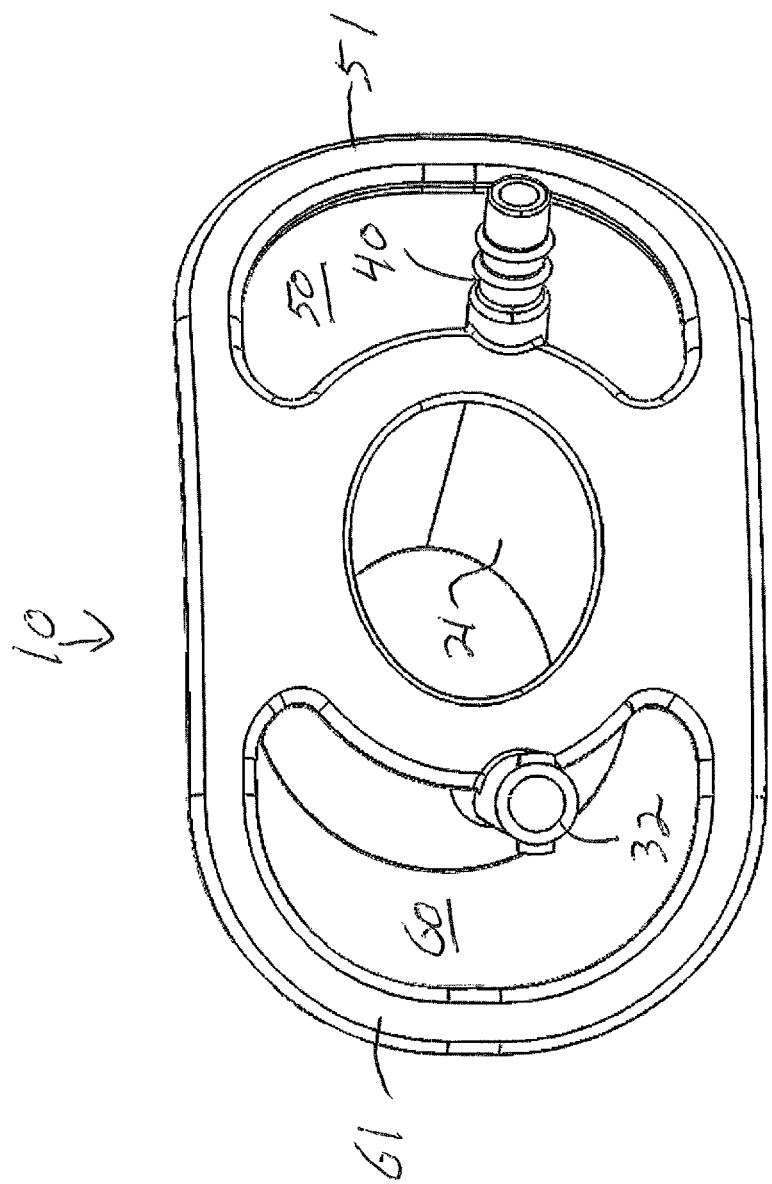
FIG. 2 is a right front perspective view of the surgical airway device of FIG. 1.
Figure 3:
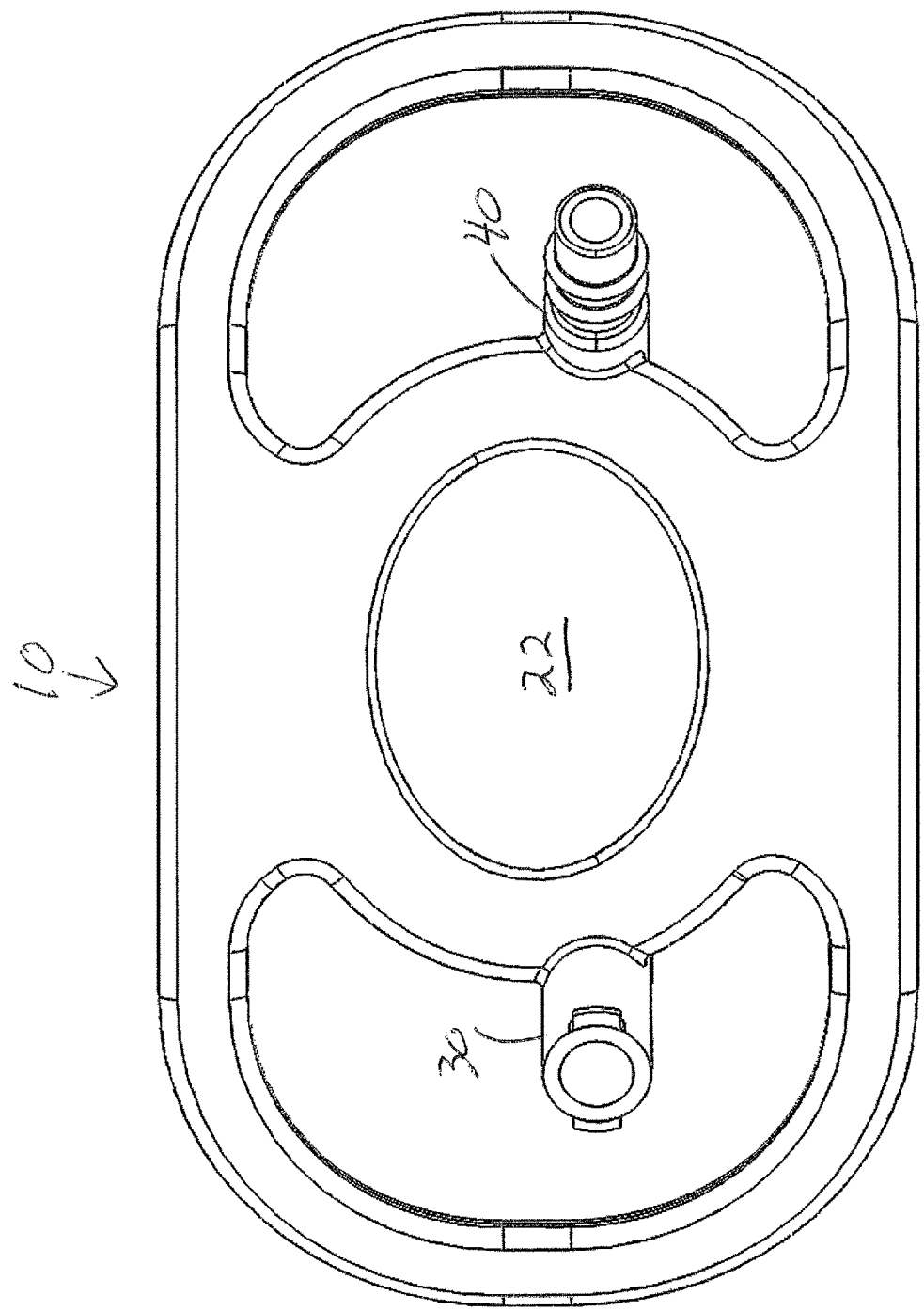
FIG. 3 is a front view of the surgical airway device of FIG. 1.
Figure 4:
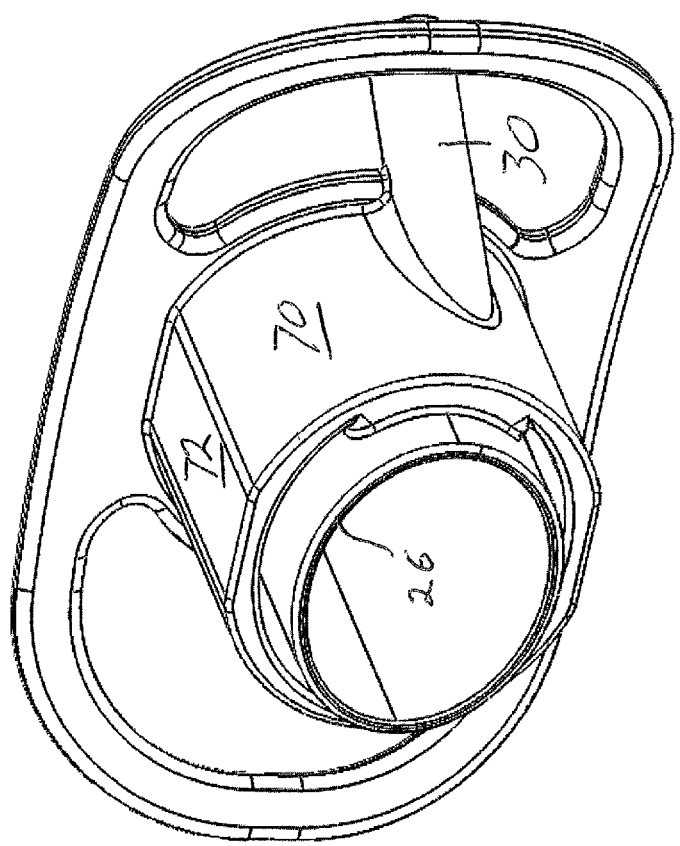
FIG. 4 is a right side rear perspective view of the surgical airway device of FIG. 1.
Figure 5:
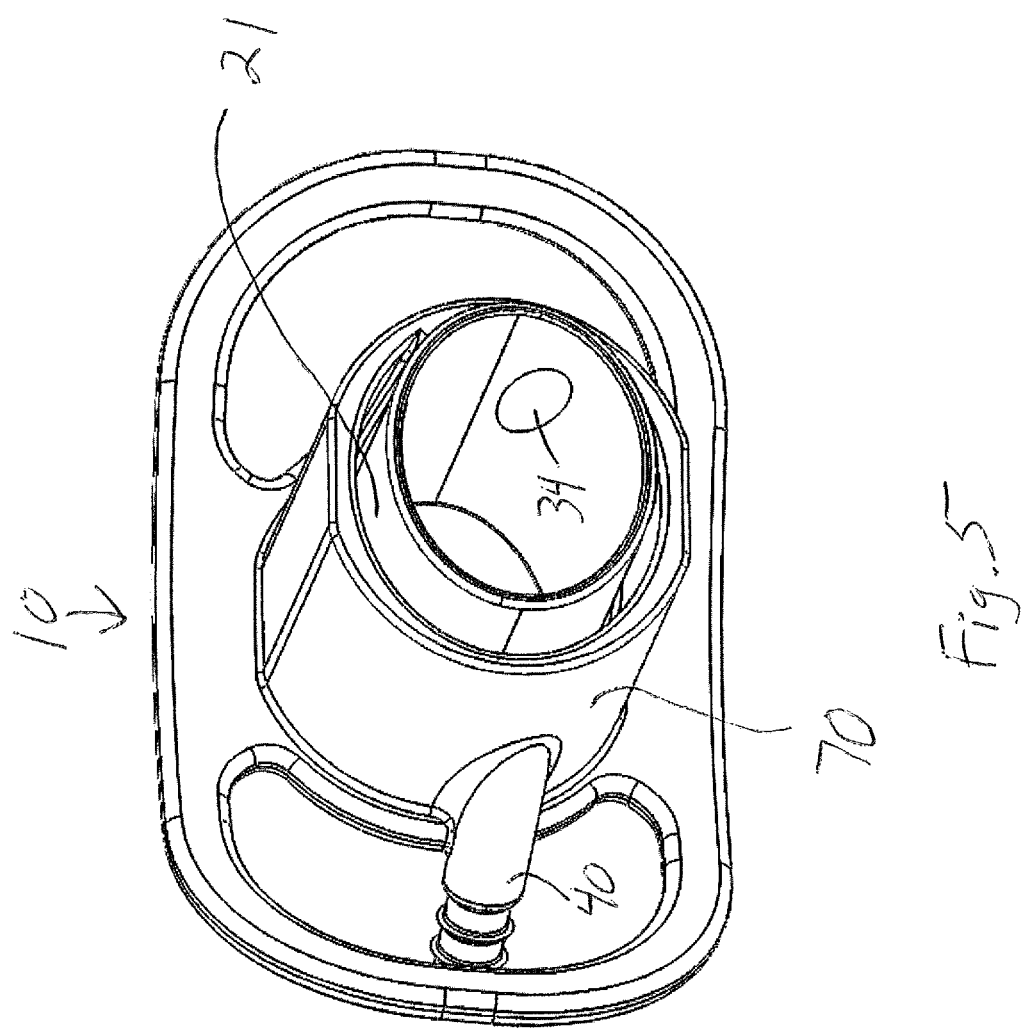
FIG. 5 is a left side rear perspective view of the surgical airway device of FIG. 1.
Figure 6:
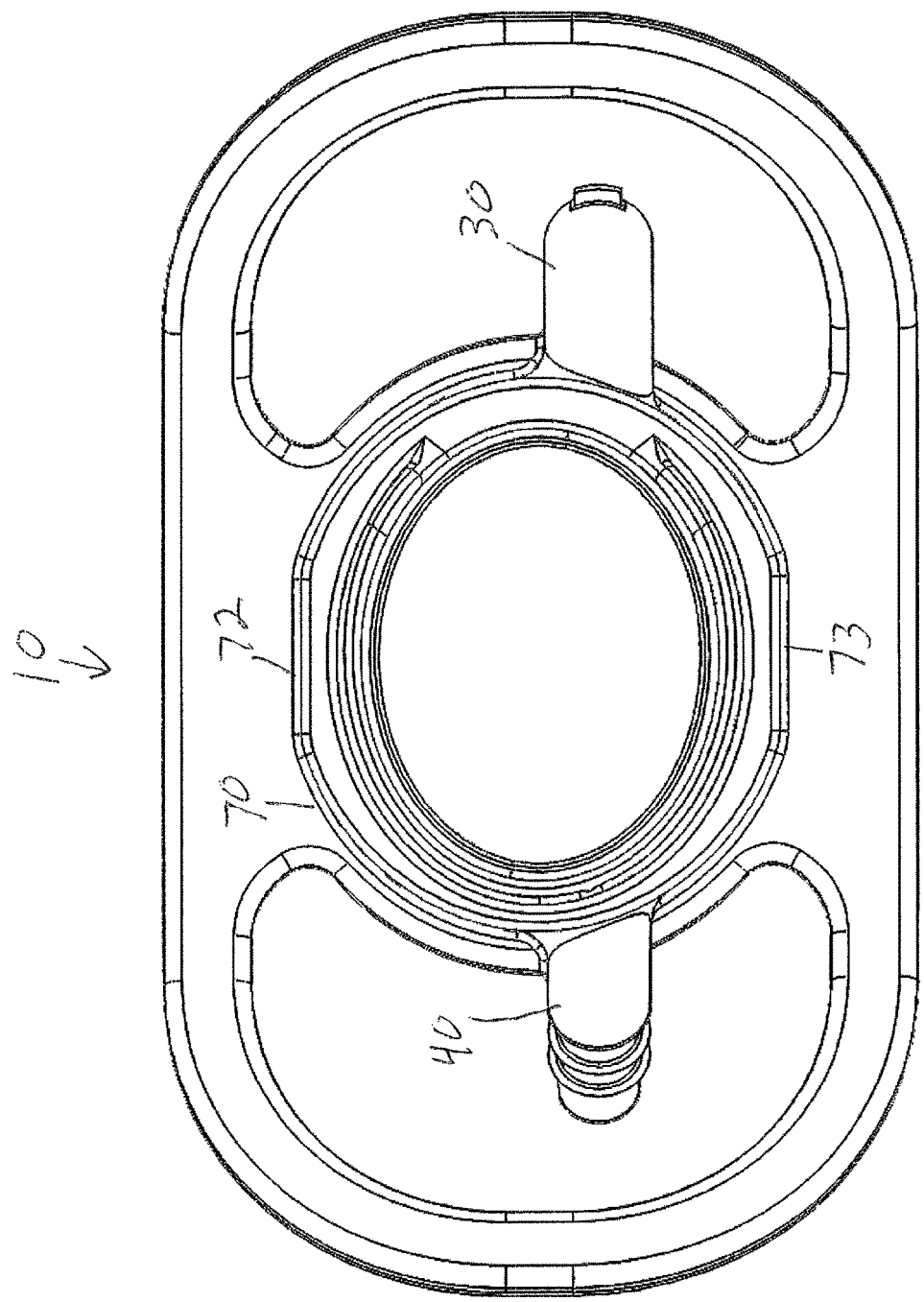
FIG. 6 is a rear view of the surgical airway device of FIG. 1.
Figure 7:
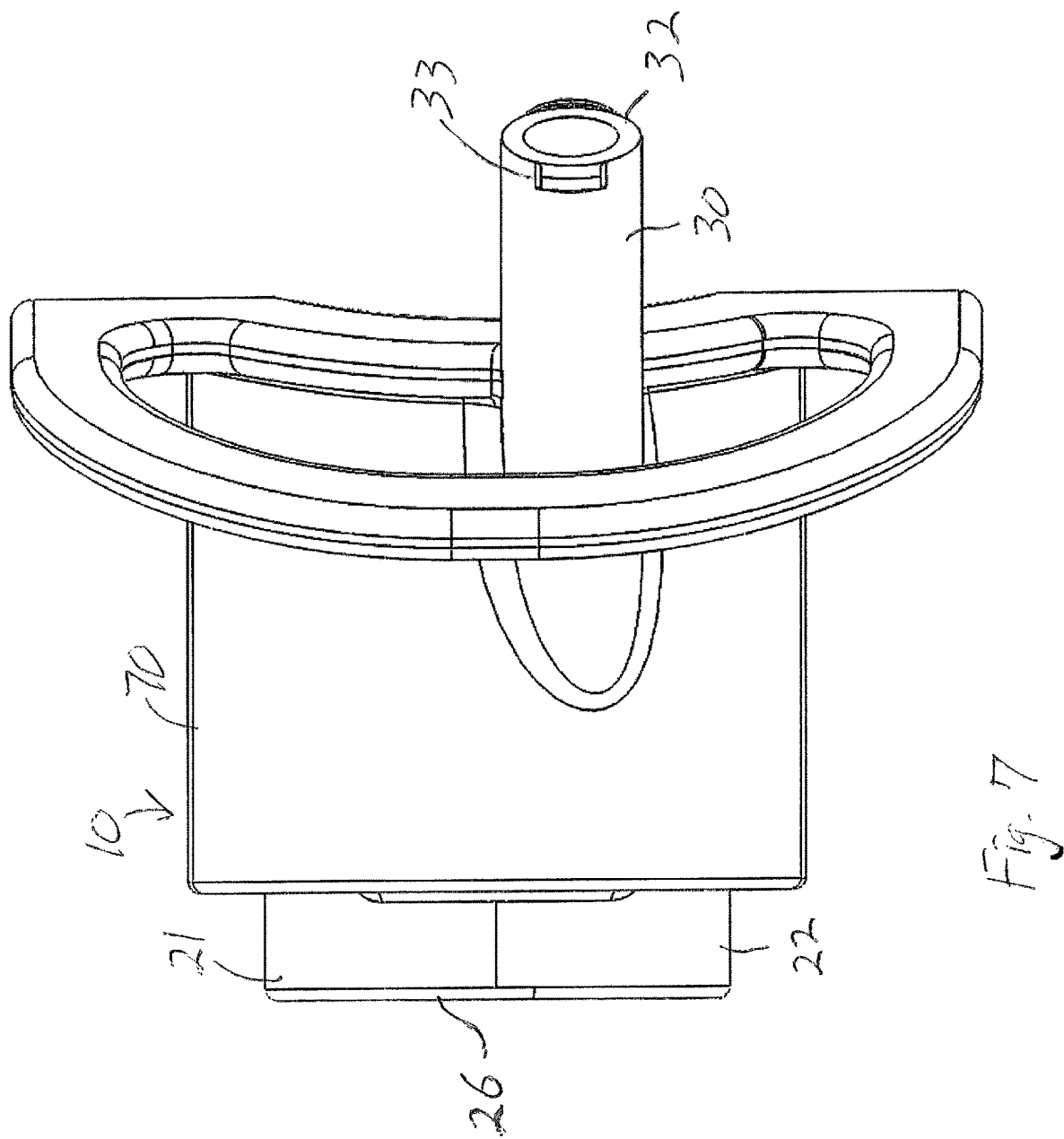
FIG. 7 is a right side view of the surgical airway device of FIG. 1.
Figure 8:
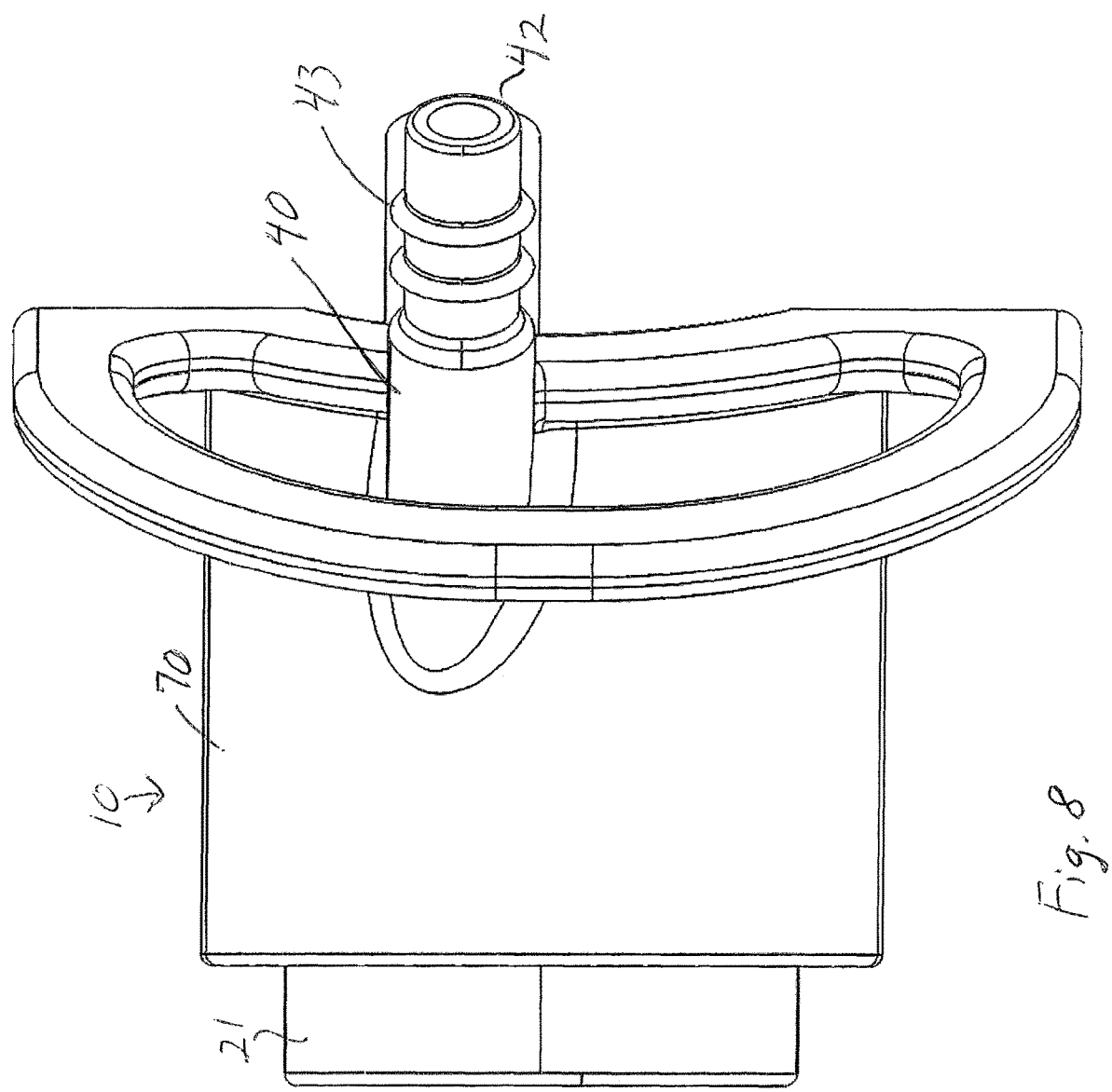
FIG. 8 is a left side view of the surgical airway device of FIG. 1.

Bite block/surgical airway device 10 is in one non-limiting example a unitary injection molded plastic structure that can be made from polypropylene or other known materials. Device 10 maintains an airway in a surgical patient and also is useful for capnography as well as aspiration of saliva to help maintain the continuous utility of scopes and other instruments that are inserted into the patient through the mouth via the central working channel 22 of device 10.

Device 10 includes anterior peripheral flange 20 that is constructed and arranged to be located outside of the patient's mouth, close to or against the lips. Inner tube 21 is a generally cylindrical tube with anterior rim and opening 24 and posterior rim and opening 26. Inner tube 21 defines working channel 22 that can have a size and shape that is appropriate for the patient (e.g., child or adult) as well as an appropriate diameter so that it can accommodate the device or devices that are meant to be inserted into the mouth through working channel 22. In one example, inner tube 21 is a straight, generally oval-shaped tube as shown in the drawings. Tube 21 may have a diameter across its major axis of 60 Fr (which equals 20 millimeters).

Figure 12:
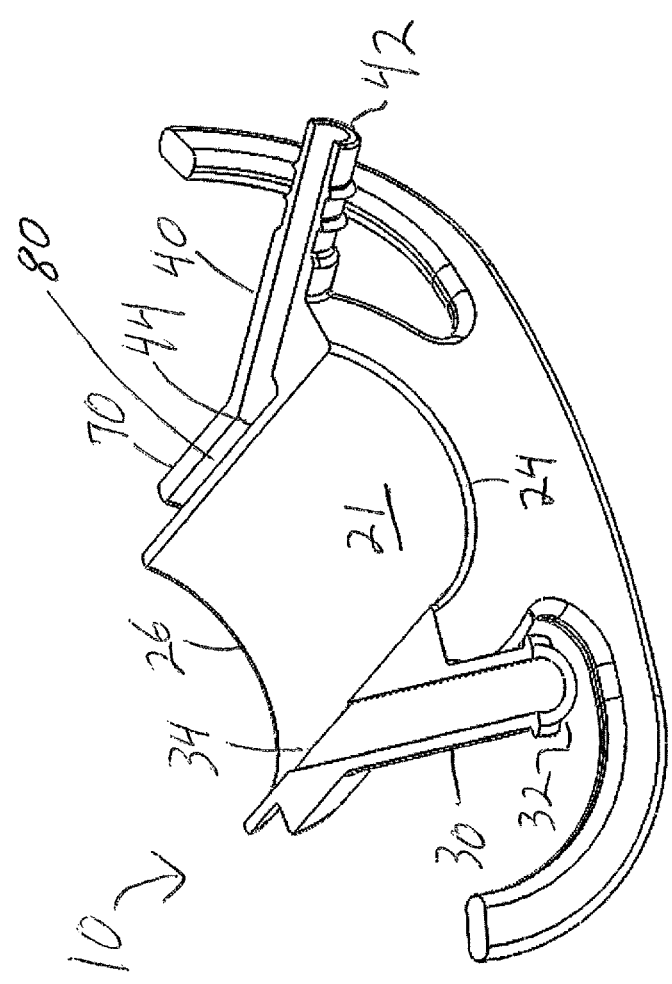
FIG. 12 is a horizontal mid-line cross-sectional right front perspective view of the surgical airway device of FIG. 1.

Device 10 includes structure that allows the device to be used for capnography. In this non-limiting example, the structure comprises right-side lumen 30 that has anterior rim and opening 32 that projects in front of flange 20 and posterior rim and opening 34 that fluidly communicates with working channel 22. Opening 34 is preferably located posteriorly in channel 22, e.g., closer to posterior end 26 than to anterior end 24. See FIG. 12. In this example, lumen 30 defines an anterior female luer lock fitting 33 that can be connected to a standard luer lock inlet to a carbon dioxide monitoring device, so that the device can be used for capnography.

Device 10 also includes left-side lumen 40 with anterior rim/opening 42 and posterior rim/opening 44. Shown in this non-limiting embodiment is a barbed fitting 43; fitting 43 can vary in size, and is designed as a typical barbed fitting that is constructed and arranged to accept and grip standard flexible medical tubing. One use of lumen 40 is for saliva aspiration. Features of device 10 are designed to channel saliva into opening 44 into lumen 40. This is accomplished as follows. Device 10 includes outer tube 70 that is generally coaxial with and fully or partially surrounds inner tube 21. Outer tube 70 is spaced from inner tube 21 along the left side contiguous with lumen 40, to define coaxial gap 80. Tube 70 defines top and bottom flat areas 72 and 73, respectively, that provide bite surfaces to help to maintain the device in the mouth and in the proper orientation in the mouth in the location shown in the drawings (with lumen 40 on the left side of the patient, which is typically located at the lowest point during surgery).

Figure 9:
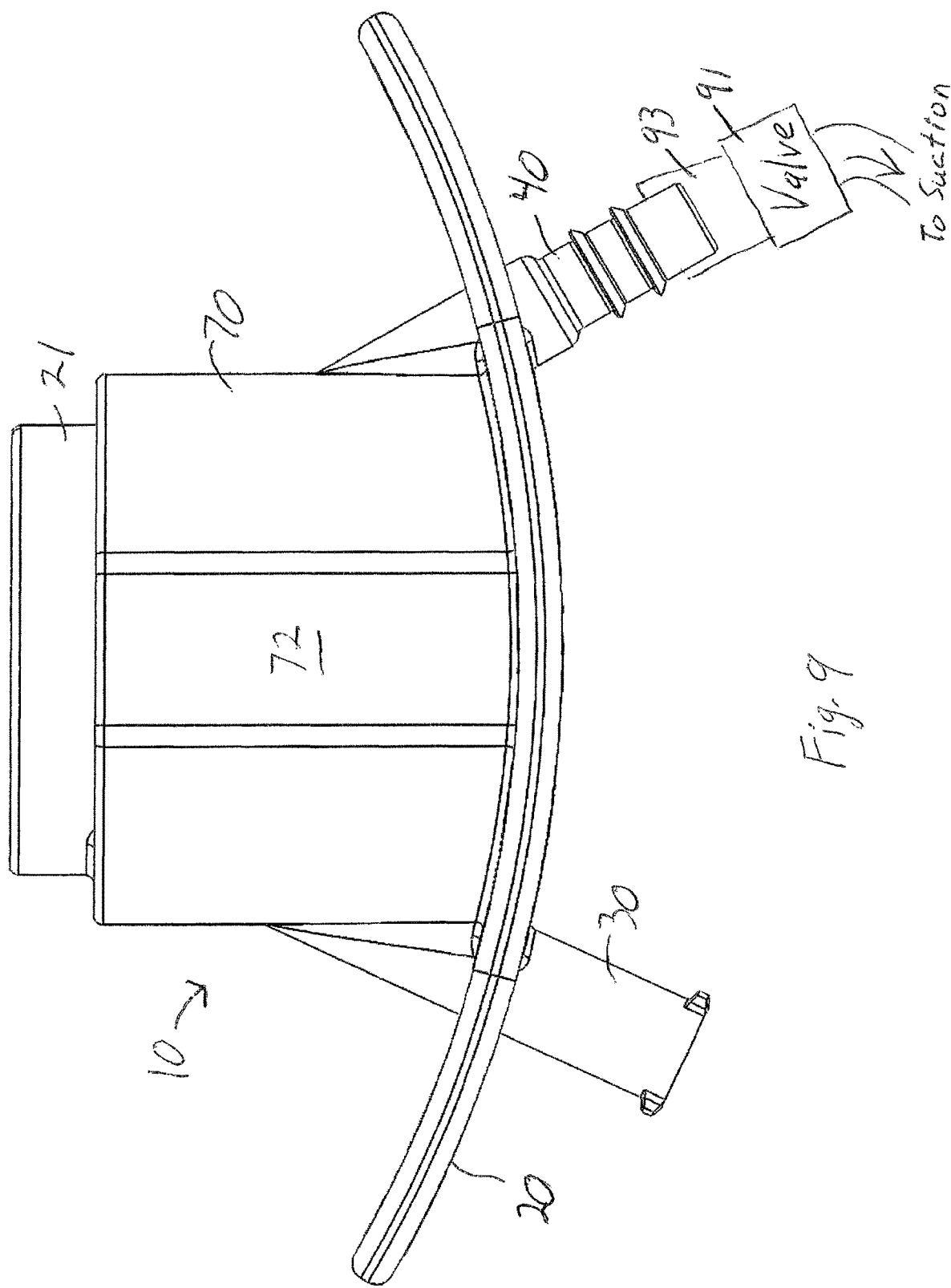
FIG. 9 is a top view of the surgical airway device of FIG. 1.
Figure 10:
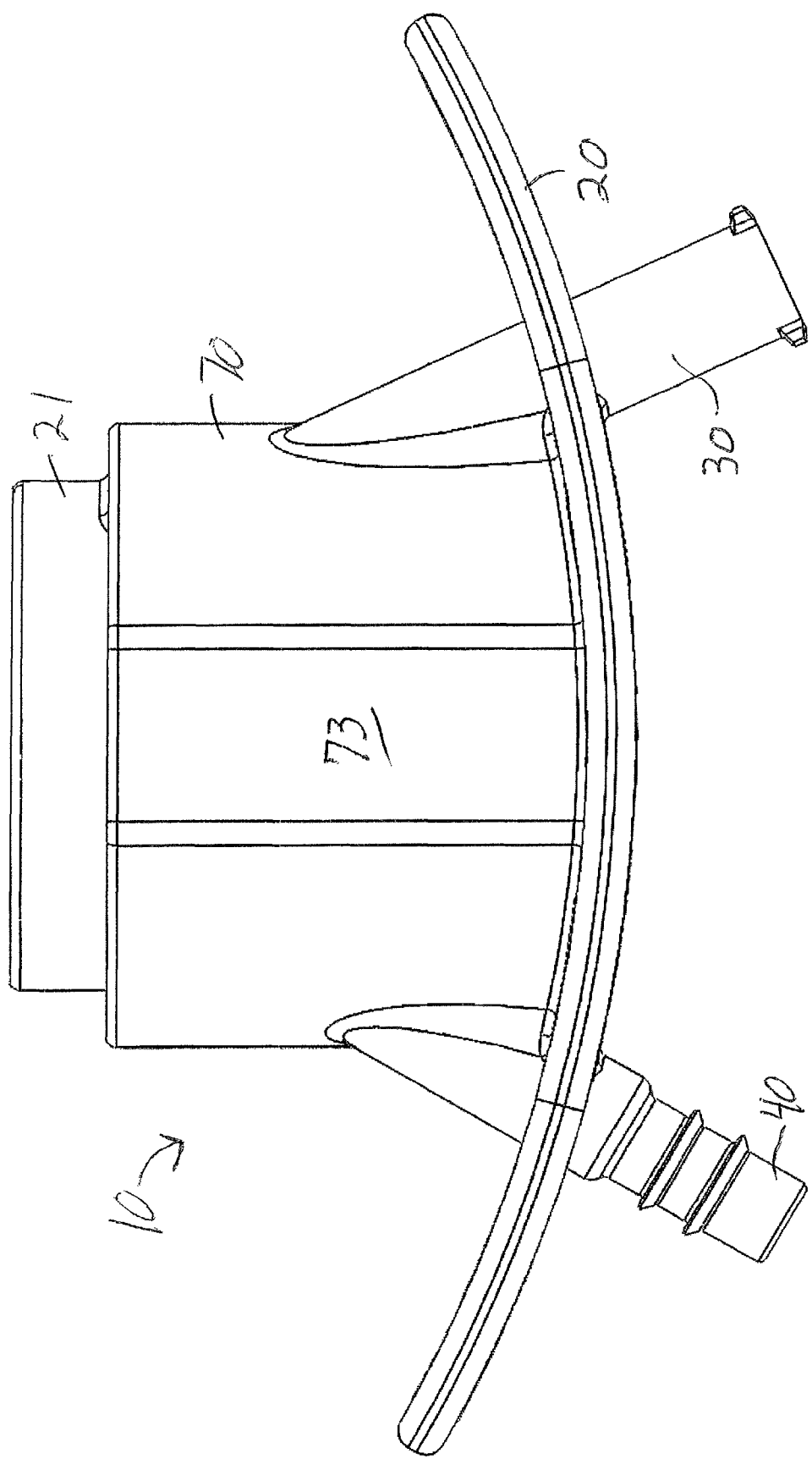
FIG. 10 is a bottom view of the surgical airway device of FIG. 1.
Figure 11:
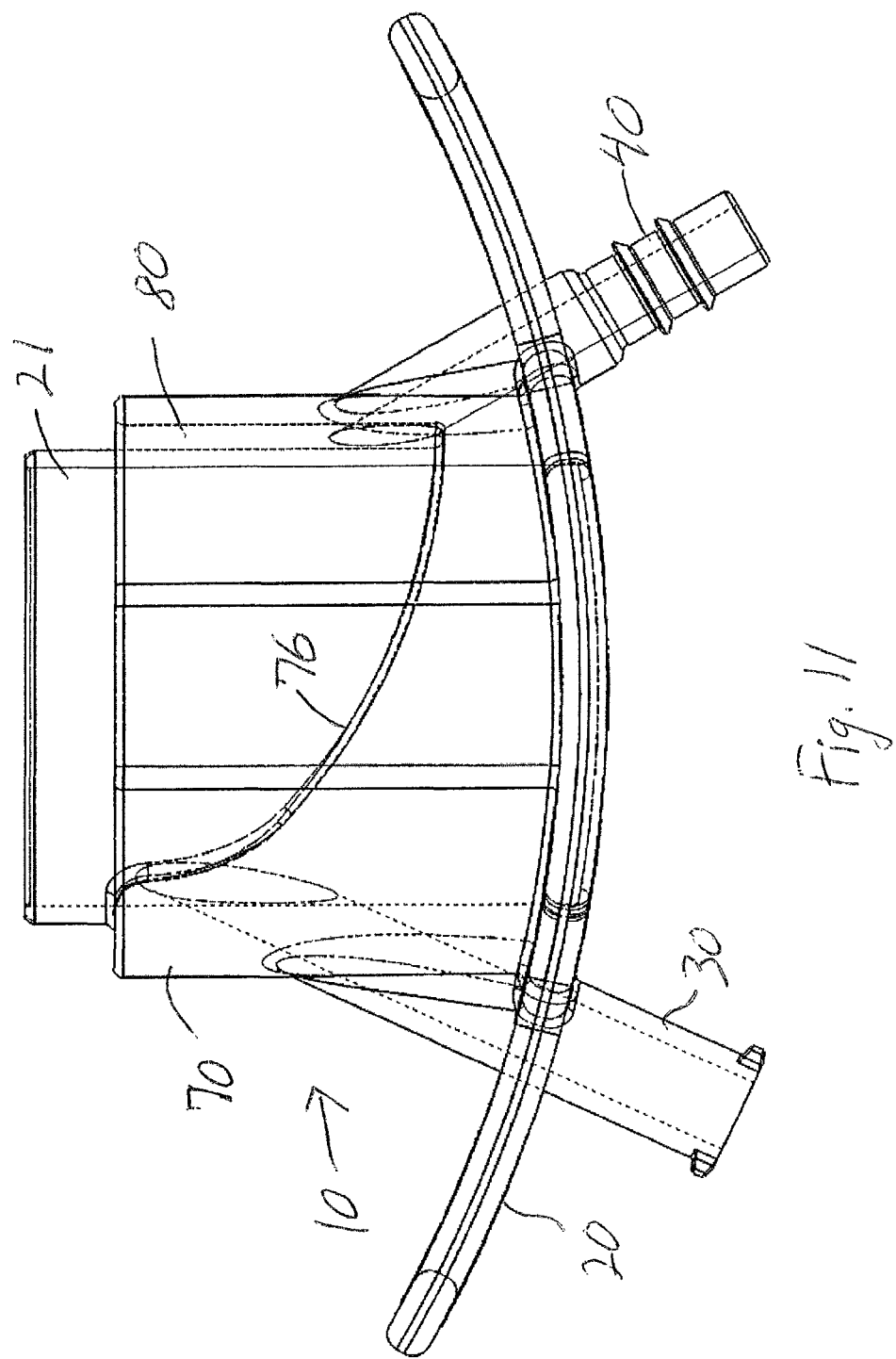
FIG. 11 is a top view of the surgical airway device of FIG. 1, illustrating hidden features in dashed line.

In use, device 10 is placed in the patient's mouth. The patient typically lies on the left side, thus the left side of the mouth is down. Saliva will thus drain to the left. When a vacuum source (not shown) is coupled to lumen 40, saliva can be sucked through lumen 40 and out of the mouth. Partially annular coaxial gap 80 between tube 70 and channel 22 allows for the collection and drainage of saliva into lumen opening 44. Curved posterior gap inner wall 76 (best shown in FIG. 11) terminates at the anterior end of opening 44. Saliva can thus drain along surface 76 and be directed into lumen 40. The suction applied to lumen 40 can be continuous, or a known "chimney"-type valve (such as disclosed in U.S. Pat. No. 4,534,542) or the like 91, FIG. 9, can be included in line (e.g., in line with tubing 93) to allow manual control over the suction. Lumens 30 and 40 are preferably located at or more preferably below the horizontal midline of the surgical airway device (the horizontal midline in the case of the example shown in FIGS. 1-13 is collinear with the major axis of oval-shaped working channel 22). Placement of the lumens below the centerline provides more room for the surgeon to manipulate a scope located in channel 22.

Lumen 40 can alternatively be used for oxygen delivery, in which case the oxygen enters the throat via the posterior end of gap 80, which is preferably posterior to the capnography inlet 34 and thus is less likely to affect the capnography results. Most times, though, oxygen is supplied to a patient through a nasal cannula, so lumen 40 can be used for saliva aspiration.

An alternative to the lumen construction illustrated in FIGS. 1-13 would be to construct the anterior ends of the lumen(s) as open tubes, without a particular fitting. In this case the product supplier could bond an off-the-shelf appropriate fitting for the particular application to the end of the lumen. For example, FIG. 14 illustrates surgical airway device 10a with open side ports 30a and 40a that are ready to receive male slip fittings. Examples of male slip fittings include male slip to female Luer lock fittings, and male slip to barbed fittings, which can be used to create the same result as the embodiment of FIGS. 1-13. The ports can project different lengths forward of flange or shield 20 as desired to accept a particular type of fitting and/or such that the fitting is properly located relative to the flange.

Flange 20 in this non-limiting example defines crescent-shaped openings 50 and 60 that can be used to allow access into the mouth; for example, a finger to position an instrument and/or one or more other instruments. Remaining crescent-shaped peripheral rims 51 and 61 provide locations for attachment of a strap or other structure to hold device 10 in the patient's mouth. As one example of a construction that is adapted to be coupled to an elastic strap, enlarged-head posts 62 and 63, FIG. 14, can be included. Other mechanical structures to couple to a strap could be used instead.

Results of the subject device include a removal of saliva thus decreasing the likelihood that scope optics will be fouled with saliva, which normally requires the optics to be removed and cleaned. Also the patient is less likely to gag or aspirate their own saliva into their lungs. Further, continuous suction and capnography can be accomplished without interruption of the procedure or interruption of oxygen delivery.

Another example of a surgical airway device 10b is shown in FIGS. 15 and 16. Device 10b includes a sheath 102 that can be placed inside of inner tube 21, in working channel 22, to establish an unobstructed path for gas exchange and/or a pathway to help insert a fiber optic scope and/or endotracheal tube or other device that needs to be inserted through the mouth. Sheath 102 has posterior end 110 that projects beyond posterior rim 26 of inner tube 21. Sheath 102 is constructed like a rescue airway. The sheath includes open side 108 of curved tube 104; side 108 is aligned with opening 34 so that capnography is not interrupted. This function of open side 108 could alternatively be accomplished with an opening that did not extend the full length of tube 104, e.g., a smaller opening that was aligned with opening 34. Anterior flange 106 sits against the face of flange 22 around rim 24. The design of sheath 102 is such that it does not reduce or limit the function of the two ports 30 and 40. Additionally, the interior diameter of the sheath along with the cut-away side feature allow the physician to place a scope or endotracheal tube and then remove the bite block and sheath if desired.

Although features of the disclosure are shown in some drawings and not others, this is not a limitation of the scope of the invention, which is defined by the claims. Other aspects, features and advantages will occur to those skilled in the field.

What is claimed is:

1. A surgical airway device that is constructed and arranged to be placed into the mouth of a patient, to maintain a surgical airway in the patient, the surgical airway device comprising:
    a flange constructed and arranged to be located outside of the patient's mouth;
    an inner tube that defines a working channel inside of the inner tube, wherein the working channel comprises an anterior opening in the flange and configured to be located proximate the patient's lips, and a posterior end configured to be located in the back of the patient's mouth;
    an outer tube that is generally coaxial with, spaced from and fully or partially surrounds the inner tube, wherein a coaxial gap is located between at least part of the outer tube and the inner tube;
    a first lumen that is in direct fluid communication with the working channel and not the coaxial gap, wherein the first lumen passes through the outer tube and the inner tube and defines a first lumen opening in the inner tube that is open to the working channel; and
    a second lumen that is in direct fluid communication with the coaxial gap and not the working channel, wherein the second lumen passes through the outer tube and defines a second lumen opening in the outer tube that is open to the coaxial gap.

2. The surgical airway device of claim 1 wherein the inner tube has a left side that is configured to be on the left side of the patient when the surgical airway device is placed into the patient's mouth, and wherein the second lumen is on the left side of the inner tube when the surgical airway device is placed in the patient's mouth.

3. The surgical airway device of claim 2 wherein the second lumen is adapted to be connected to at least one of a source of suction and a source of oxygen.

4. The surgical airway device of claim 3 further comprising a suction control device located between the second lumen and the source of suction to which the second lumen is adapted to be connected to.

5. The surgical airway device of claim 1 wherein the inner tube has a right side that is configured to be on the right side of the patient when the surgical airway device is placed into the patient's mouth, and wherein the first lumen is on the right side of the inner tube when the device is placed in the patient's mouth.

6. The surgical airway device of claim 5 wherein the first lumen is adapted to be connected to a carbon dioxide monitor.

7. The surgical airway device of claim 1 further comprising a curved wall bordering at least part of the coaxial gap, to help direct saliva into the second lumen.

8. The surgical airway device of claim 1 wherein the surgical airway device defines a lateral midline and wherein the two lumens are located at or below the midline.

9. The surgical airway device of claim 1 further comprising a sheath located in the working channel and with a sheath opening that is in fluid communication with the first lumen.

10. The surgical airway device of claim 9 wherein the sheath has a posterior end that projects beyond the posterior end of the inner tube.

11. The surgical airway device of claim 10 wherein the sheath comprises a sheath flange that sits against the flange of the surgical airway device and a curved sheath tube that is located in the inner tube and has a posterior end that projects beyond the posterior end of the inner tube.

12. The surgical airway device of claim 11 wherein the sheath opening comprises an open side in the sheath tube, wherein the open side also extends through the sheath flange.

13. A surgical airway device that is constructed and arranged to be placed into the mouth of a patient, to maintain a surgical airway in the patient, the surgical airway device comprising:
   a flange constructed and arranged to be located outside of the patient's mouth;
   an inner tube that defines a working channel inside of the inner tube, wherein the working channel comprises an anterior opening in the flange and configured to be located proximate the patient's lips, and a posterior end configured to be located in the back of the patient's mouth;
   an outer tube that is generally coaxial with, spaced from and fully or partially surrounds the inner tube, wherein a coaxial gap is located between at least part of the outer tube and the inner tube;
   a first lumen that is in direct fluid communication with the working channel and not the coaxial gap, wherein the inner tube has a right side that is configured to be on the right side of the patient when the surgical airway device is placed into the patient's mouth, and wherein the first lumen is on the right side of the inner tube when the device is placed in the patient's mouth and wherein the first lumen is adapted to be connected to a carbon dioxide monitor, wherein the first lumen passes through the outer tube and the inner tube and defines a first lumen opening in the inner tube that is open to the working channel; and
   a second lumen that is in direct fluid communication with the coaxial gap and not the working channel, wherein the inner tube has a left side that is configured to be on the left side of the patient when the surgical airway device is placed into the patient's mouth, and wherein the second lumen is on the left side of the inner tube when the surgical airway device is placed in the patient's mouth and wherein the second lumen is adapted to be connected to at least one of a source of suction and a source of oxygen, wherein the second lumen passes through the outer tube and defines a second lumen opening in the outer tube that is open to the coaxial gap;
   wherein the surgical airway device defines a lateral midline and wherein the two lumens are located at or below the midline.

14. The surgical airway device of claim 13 further comprising a sheath located in the working channel and with an opening that is in fluid communication with the first lumen, wherein the sheath has a posterior end that projects beyond the posterior end of the inner tube.

15. A method of accomplishing an airway, a scope working channel, at least one of posterior saliva suction and oxygen delivery, and anterior capnography in a patient, comprising:
   a) providing a surgical airway device for maintaining a surgical airway in a patient, the surgical airway device comprising:
      i) a flange constructed and arranged to be located outside of the patient's mouth;
      ii) an inner tube that defines a working channel inside of the inner tube, wherein the working channel comprises an anterior opening in the flange and configured to be located proximate the patient's lips, and a posterior end configured to be located in the back of the patient's mouth;
      iii) an outer tube that is generally coaxial with, spaced from and fully or partially surrounds the inner tube, wherein a coaxial gap is located between at least part of the outer tube and the inner tube;
      iv) a first lumen that is in direct fluid communication with the working channel and not the coaxial gap, wherein the first lumen passes through the outer tube and the inner tube and defines a first lumen opening in the inner tube that is open to the working channel; and
      v) a second lumen that is in direct fluid communication with the coaxial gap and not the working channel, wherein the second lumen passes through the outer tube and defines a second lumen opening in the outer tube that is open to the coaxial gap;
   b) inserting the surgical airway device into the patient's mouth such that the flange is located outside of and against or very close to the patient's lips;
   c) fluidly coupling a carbon dioxide monitoring device to the first lumen; and
   d) fluidly coupling a suction source or an oxygen delivery source to the second lumen.

16. The method of claim 15 wherein the inner tube has a left side that is configured to be on the left side of the patient when the surgical airway device is placed into the patient's mouth, and wherein the second lumen is on the left side of the inner tube when the device is placed in the patient's mouth.

17. The method of claim 16 wherein the surgical airway device further comprises a suction control device located between the second lumen and the source of suction to which the second lumen is adapted to be connected to.

18. The method of claim 15 wherein the inner tube has a right side that is configured to be on the right side of the patient when the surgical airway device is placed into the patient's mouth, and wherein the first lumen is on the right side of the inner tube when the surgical airway device is placed in the patient's mouth.

19. The method of claim 15 wherein the surgical airway device further comprises a curved wall bordering at least part of the coaxial gap, to help direct saliva into the second lumen.

20. A method of accomplishing an airway, a scope working channel, at least one of posterior saliva suction and oxygen delivery, and anterior capnography in a patient, comprising:
   a) providing a surgical airway device for maintaining a surgical airway in a patient, the surgical airway device comprising:
      i) a flange constructed and arranged to be located outside of the patient's mouth;
      ii) an inner tube that defines a working channel inside of the inner tube, wherein the working channel comprises an anterior opening in the flange and located proximate the patient's lips, and a posterior end located in the back of the patient's mouth;
      iii) an outer tube that is generally coaxial with, spaced from and fully or partially surrounds the inner tube, wherein a coaxial gap is located between at least part of the outer tube and the inner tube;
      iv) a curved wall bordering at least part of the coaxial gap, to help direct saliva into a second lumen;

v) wherein the inner tube has a right side that is configured to be on the right side of the patient when the surgical airway device is placed into the patient's mouth, and wherein a first lumen is on the right side of the inner tube when the surgical airway device is placed in the patient's mouth and is in direct fluid communication with the working channel and not the coaxial gap, wherein the first lumen passes through the outer tube and the inner tube and defines a first lumen opening in the inner tube that is open to the working channel; and vi) wherein the inner tube has a left side that is configured to be on the left side of the patient when the surgical airway device is placed into the patient's mouth, and wherein the second lumen is on the left side of the inner tube when the device is placed in the patient's mouth and is in direct fluid communication with the coaxial gap and not the working channel, wherein the second lumen passes through the outer tube and defines a second lumen opening in the outer tube that is open to the coaxial gap;

b) inserting the surgical airway device into the patient's mouth such that the flange is located outside of and against or very close to the patient's lips;

c) fluidly coupling a carbon dioxide monitoring device to the first lumen; and d) fluidly coupling a suction source to the second lumen.

21. The surgical airway device of claim 1, wherein the first lumen opening in the inner tube is closer to the posterior end of the working channel than it is to the anterior end of the working channel.

22. A surgical airway device that is constructed and arranged to be placed into the mouth of a patient, to maintain a surgical airway in the patient, the surgical airway device comprising:

a flange constructed and arranged to be located outside of the patient's mouth;

an inner tube that defines a working channel inside of the inner tube, wherein the working channel comprises an anterior opening in the flange and configured to be located proximate the patient's lips, and a posterior end configured to be located in the back of the patient's mouth;

an outer tube that is generally coaxial with, spaced from and fully or partially surrounds the inner tube, wherein a coaxial gap is located between at least part of the outer tube and the inner tube;

a first lumen that is in direct fluid communication with the working channel and not the coaxial gap;

a second lumen that is in direct fluid communication with the coaxial gap and not the working channel; and a sheath located in the working channel and with a sheath opening that is in fluid communication with the first lumen, wherein the sheath has a posterior end that projects beyond the posterior end of the inner tube, wherein the sheath comprises a sheath flange that sits against the flange of the surgical airway device and a curved sheath tube that is located in the inner tube and has a posterior end that projects beyond the posterior end of the inner tube, wherein the sheath opening comprises an open side in the sheath tube, and wherein the open side also extends through the sheath flange.

* * * * *